(12) United States Patent
Anderson

(10) Patent No.: US 9,808,284 B2
(45) Date of Patent: Nov. 7, 2017

(54) PROSTHESIS MANIPULATION POUCH

(71) Applicant: Noah Robert Anderson, San Francisco, CA (US)

(72) Inventor: Noah Robert Anderson, San Francisco, CA (US)

(73) Assignee: Robert G. Anderson, Aledo, TX (US)

( * ) Notice: Subject to any disclaimer, the term of this patent is extended or adjusted under 35 U.S.C. 154(b) by 420 days.

(21) Appl. No.: 14/591,472

(22) Filed: Jan. 7, 2015

(65) Prior Publication Data

US 2015/0126812 A1 May 7, 2015

(51) Int. Cl.

| | |
|---|---|
| A61B 17/02 | (2006.01) |
| A61B 17/34 | (2006.01) |
| A61F 2/12 | (2006.01) |
| A61F 2/00 | (2006.01) |
| A61B 17/00 | (2006.01) |
| A61B 90/40 | (2016.01) |

(52) U.S. Cl.
CPC .......... *A61B 17/3468* (2013.01); *A61B 17/02* (2013.01); *A61B 17/0293* (2013.01); *A61B 17/3423* (2013.01); *A61F 2/0095* (2013.01); *A61F 2/12* (2013.01); *A61B 90/40* (2016.02); *A61B 2017/0046* (2013.01); *A61B 2017/00796* (2013.01); *A61B 2017/3435* (2013.01)

(58) Field of Classification Search
CPC .................................................. A61B 17/0293
See application file for complete search history.

(56) References Cited

U.S. PATENT DOCUMENTS

| | | |
|---|---|---|
| 4,641,648 A | 2/1987 | Shapiro |
| 4,995,906 A | 2/1991 | Iwasaki et al. |
| 5,571,178 A | 11/1996 | Ledergerber |
| 5,723,006 A | 3/1998 | Ledergerber |
| 5,782,913 A | 7/1998 | Schindler et al. |
| 8,206,443 B2 | 6/2012 | Preissman |
| 8,211,173 B2 | 7/2012 | Keller et al. |
| 8,313,760 B2 | 11/2012 | Hunter |
| 8,550,090 B2 | 10/2013 | Keller et al. |
| 8,555,893 B2 | 10/2013 | Keller et al. |
| 8,641,758 B1 | 2/2014 | Anderson |
| 2007/0276484 A1 | 11/2007 | Abell et al. |
| 2009/0204107 A1 | 8/2009 | Keller et al. |

(Continued)

FOREIGN PATENT DOCUMENTS

WO  WO/2013/122568 A1  8/2013

OTHER PUBLICATIONS

Richard A. Mladick, M.D., F.A.C.S. "No-Touch" Submuscular Saline Breast Augmentation Technique, Aesthetic Plastic Surgery, 17:183-192, 1993, New York, NY.

(Continued)

*Primary Examiner* — David Bates
*Assistant Examiner* — Olivia C Chang
(74) *Attorney, Agent, or Firm* — Kirby B. Drake; Klemchuk LLP

(57) ABSTRACT

An apparatus and method for inserting prosthesis implants into a patient cavity. The apparatus includes a guide member, prosthesis manipulation pouch and a retractor. The apparatus prevents infection; prevents tears of the incision; eases insertion and placement; and provides a true no-touch operation. In use, the retractor anchors the guide member to the patient while allowing the manipulation pouch to be manipulated to force the prosthesis into a surgical cavity of a patient.

4 Claims, 8 Drawing Sheets

(56) References Cited

U.S. PATENT DOCUMENTS

Figure 1:
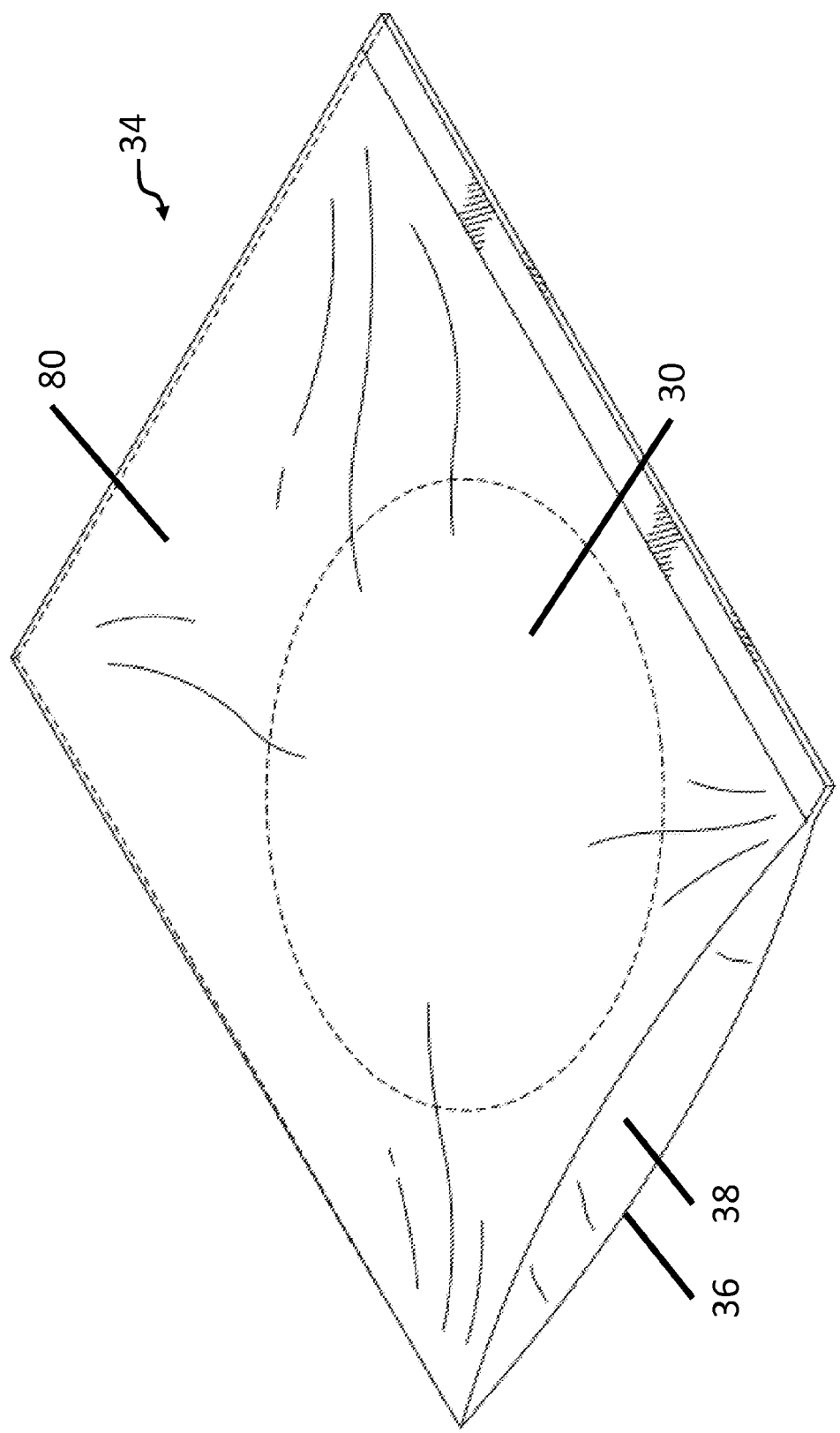

| | | |
|---|---|---|
| 2010/0280610 A1 | 11/2010 | Preissman |
| 2011/0035003 A1 | 2/2011 | Preissman |
| 2011/0218624 A1 | 9/2011 | Preissman |
| 2012/0185042 A1 | 7/2012 | Preissman |
| 2012/0259414 A1 | 10/2012 | Preissman |
| 2013/0073040 A1 | 3/2013 | Preissman |
| 2014/0074235 A1 | 3/2014 | Keller et al. |
| 2014/0074236 A1 | 3/2014 | Keller et al. |
| 2014/0148901 A1 | 5/2014 | Anderson |

OTHER PUBLICATIONS

Richard A. Mladick, M.D., F.A.C.S. Significance of *Staphylococcus epidermidis* Causing Subclinical Infection, Plastic & Reconstructive Surgery: Apr. 15, 2005—vol. 115—Issue 5—pp. 1426-1427, Virginia Beach, VA.

"Richard A. Mladick, M.D., F.A.C.S. Prevention of Capsular Contracture, Plastic & Reconstructive Surgery: May 1999—vol. 103—Issue 6—pp. 1773-1774, Virginia Beach, VA".

Thomas M. Biggs, M.D. Prefilled Saline Breast Implants Offer Significant Advantages, Aesthetic Surgery Journal Sep. 1999 vol. 19 No. 5 424, St Louis, MO.

"Mitchel H. Brown, M.D.., M.Ed. Cohesive Silicone Gel Breast Implants in Aesthetic and Reconstructive Breast Surgery,Plastic & Reconstructive Surgery: Sep. 1, 2005—vol. 116—Issue 3—pp. 768-779".

PROSTHESIS MANIPULATION POUCH

CROSS-REFERENCE TO RELATED APPLICATIONS

A claim of priority is made in this application based on Provisional Application Ser. No. 62/100,592 filed on Jan. 7, 2015 and entitled "Prosthesis Implant Device" the disclosure of which is hereby incorporated by reference in its entirety.

BACKGROUND

Field of Invention

The invention related to the apparatus and method of safely inserting a prosthesis into a human body.

Background of the Invention

The present invention is a useful and novel apparatus for assisting a surgeon to avoid complication during a surgery to implant a prosthesis, such as a breast implant, into a patient.

Breast implants are a manufactured prosthesis that are used in cosmetic and reconstructive surgery. A breast implant is gelatinous, having an outer casing or membrane and an inner fluid substance such as saline or silicone.

Most implant procedures today do not use an insertion device. The surgeon makes the incision, creates a cavity for the implant, retracts the incision and then simply manually pushes the implant into the cavity. A saline implant can be inserted into a cavity in an empty configuration; once in place in the cavity, the implant is then filled with saline solution.

Preferably, the incision in the patient is as short as possible. Shorter incisions are less unsightly. This goal of a shorter incision is easier to accomplish with a saline implant. A saline implant is relatively easy to insert through a short incision, as the bladder is unfilled and therefore small in size as it passes through the incision. In contrast, silicone implants are prefilled resulting in a more difficult and complications-susceptible operation.

The incision is made in one of four places: under the arm, in the breast fold, in the belly button, or around the nipple. Except for the belly button insertion, one incision is made for each implant. Next, the surgeon cuts a path through the tissue to the desired destination of the implant. Once that path has been created, the tissue and muscle must be separated to create a pocket, or cavity, for the implant.

The cavity may be formed in one of two places under the breast: subglandular (between the breast tissue and pectoralis muscle) or subpectoral (under the pectoralis muscle). Subglandular places the prosthesis directly behind the mammary gland and in front of the muscle. Subpectoral places the implant partially under the pectoralis major muscle. Due to the structure of the pectoralis, a portion of the implant is not covered by the pectoralis. Submuscular placement is directly behind the muscular wall of the chest.

For inflatable implants, the surgeon rolls up the implant like a cigar and pushes it through the incision and into the cavity. The surgeon then uses a tube to fill the implant with saline.

For pre-filled implants, the procedure is much the same but with a larger incision length. The implant is then manually pushed through the incision into the cavity.

Risks to patients receiving breast implants include additional surgeries to change the placement (from subglandular to subpectoral or visa versa), or to correct folding, rupture; infection; breast pain; contracted scar tissue forming around the implant; and collections of fluids around the implant. The overall complication rate is about 25% for silicone gel breast augmentation with the majority of re-operations related to implant rupture, leak or capsular contracture.

Infection, or Cellulitis, occurs in 2%-4% of patients, with some surgeons reporting much higher rates, and is usually from the bacteria normally present on the skin. Symptoms of infection include fever, pain, swelling and redness. To reduce infection, surgeons give a single dose of antibiotics before the surgery, and use an antibiotic solution in the wound before implant placement. The antibiotic solution may double as lubrication. However, surgeons can bring the rate of infection down further by eliminating the chance the prosthesis touches the skin. This "no touch" technique can be improved with prosthesis manipulation pouch of the present invention.

The implant insertion devices heretofore known suffer from a number of disadvantages:
1. Difficult to handle in a lubricious state.
2. Difficult to maintain position of insertion device in the incision.
3. Difficult to manage the speed of the insertion through the insertion or distal end of the insertion device.
4. Expensive and not re-usable.
5. Are not completely 'touch' free.
6. Have no control over external pressure applied to implant.
7. Allow the implant to come in contact with a reusable retractor which has microscopic irregularities and/or sharp edges.

SUMMARY OF THE INVENTION

An invention, which meets the needs stated above, is a system and method to insert a prosthesis into a patient. The method allows the surgeon greater control over the insertion while reducing the chance of surgical and post-surgery complications.

OBJECTS AND ADVANTAGES

Accordingly, besides the objects and advantages of the system for a breast insertion device described above, several objects and advantages of the present invention are:
a) to provide a complication-reducing method;
b) to provide a simplified insertion method;
c) to provide a controlled minimum incision length;
d) to provide a secured proximal end to the patient.

Further objects and advantages of this invention will become apparent from a consideration of the drawings and the ensuing description of the drawings.

DRAWING FIGURES

The accompanying drawings, which are incorporated in and constitute a part of this specification, illustrate embodiments of the present invention and together with the description, serve to explain the principles of this invention. In the figures:

FIG. 1: Front perspective view of a prosthesis manipulation pouch.

Figure 2:
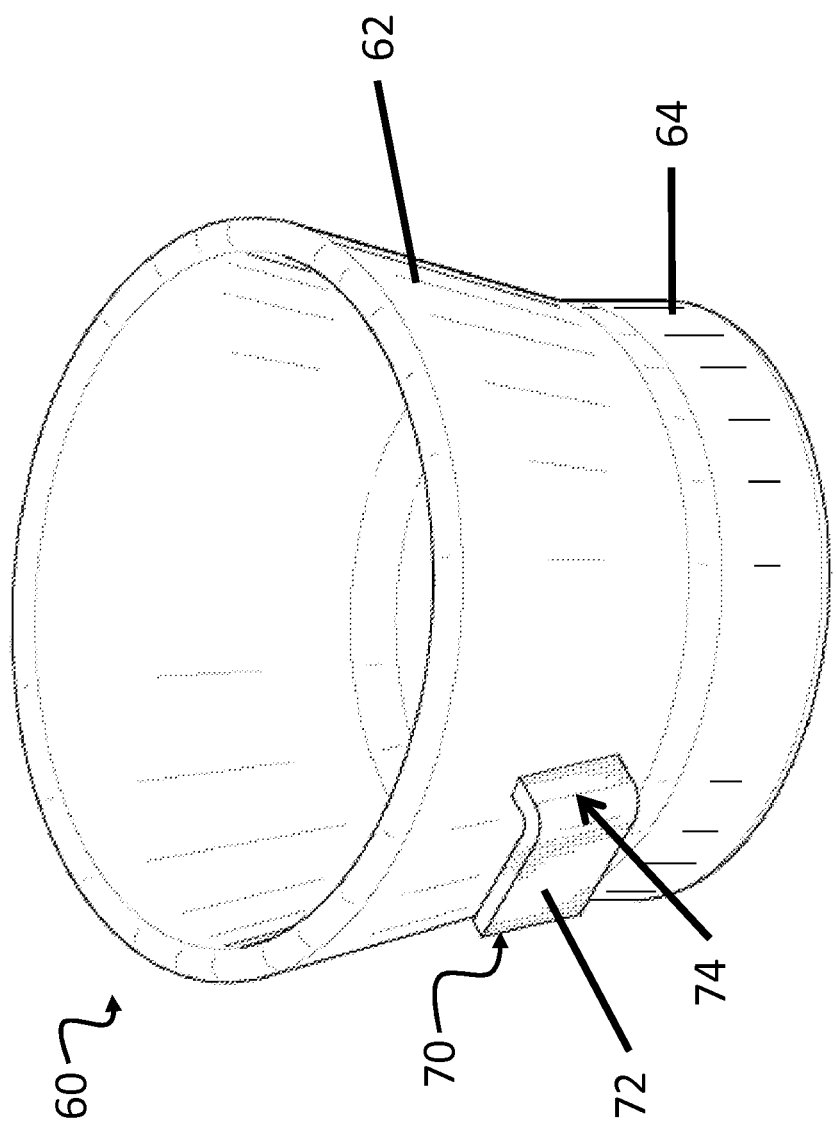

FIG. 2: Front perspective view for an implant insertion coupling device.

Figure 3:
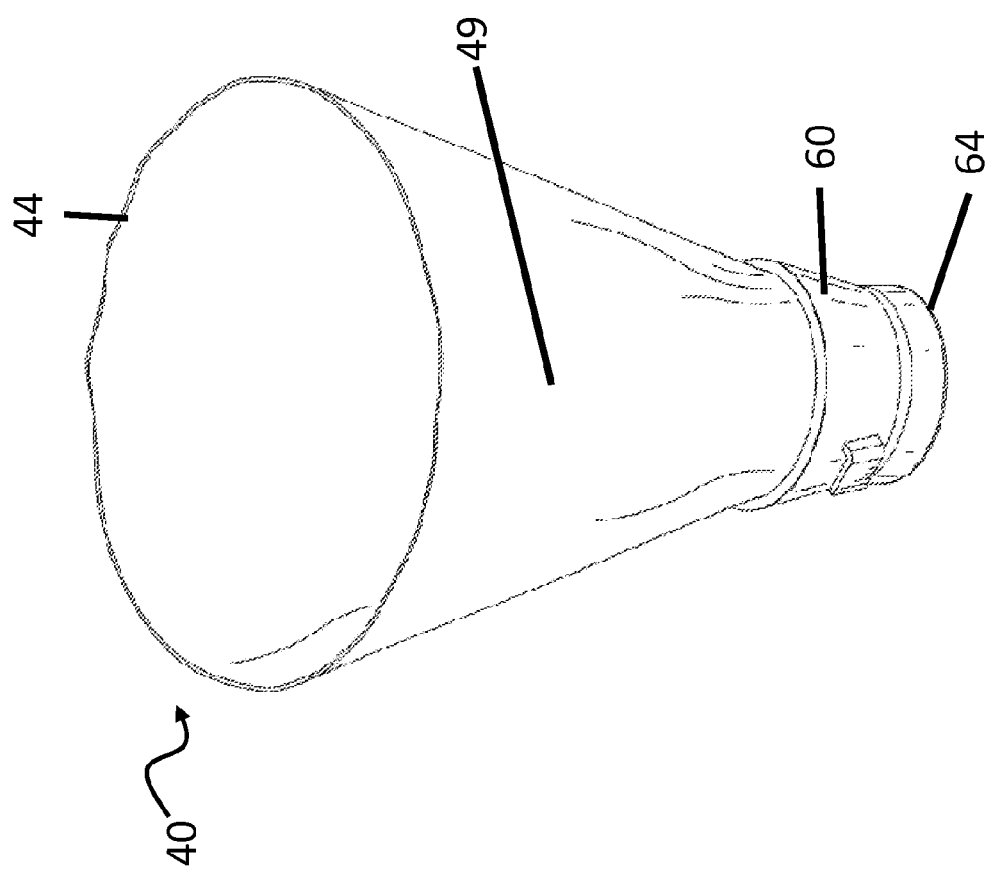

FIG. 3: Front perspective view of a short guide adapter.

Figure 4:
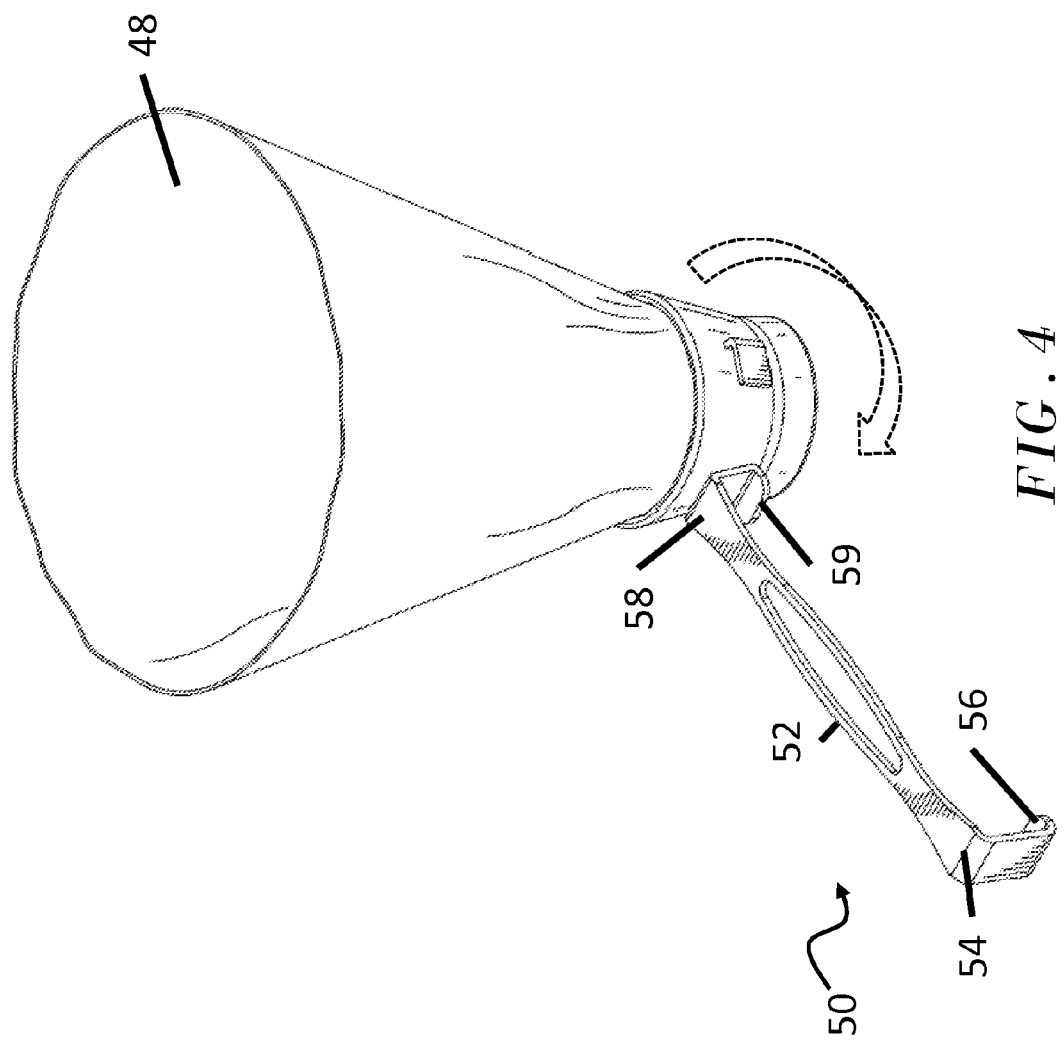

FIG. 4: Front perspective view of short guide adapter before being rotated into the coupling catch.

Figure 5:
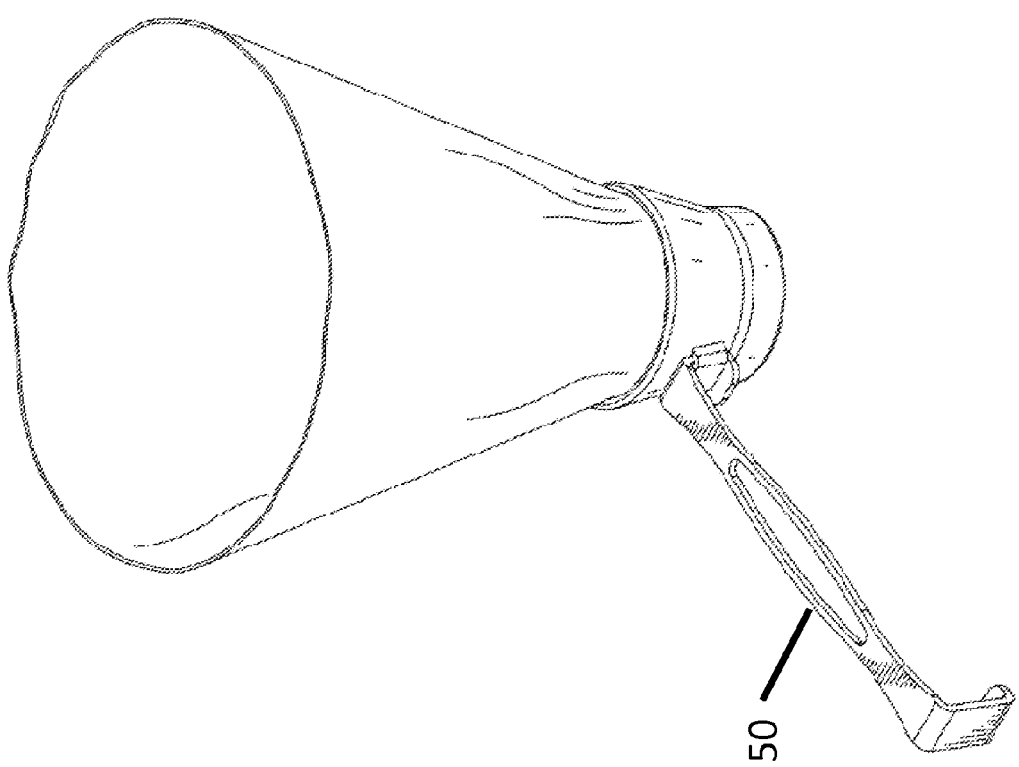

FIG. 5: Front perspective view of short guide adapter after being rotated clockwise into the coupling catch.

Figure 6:
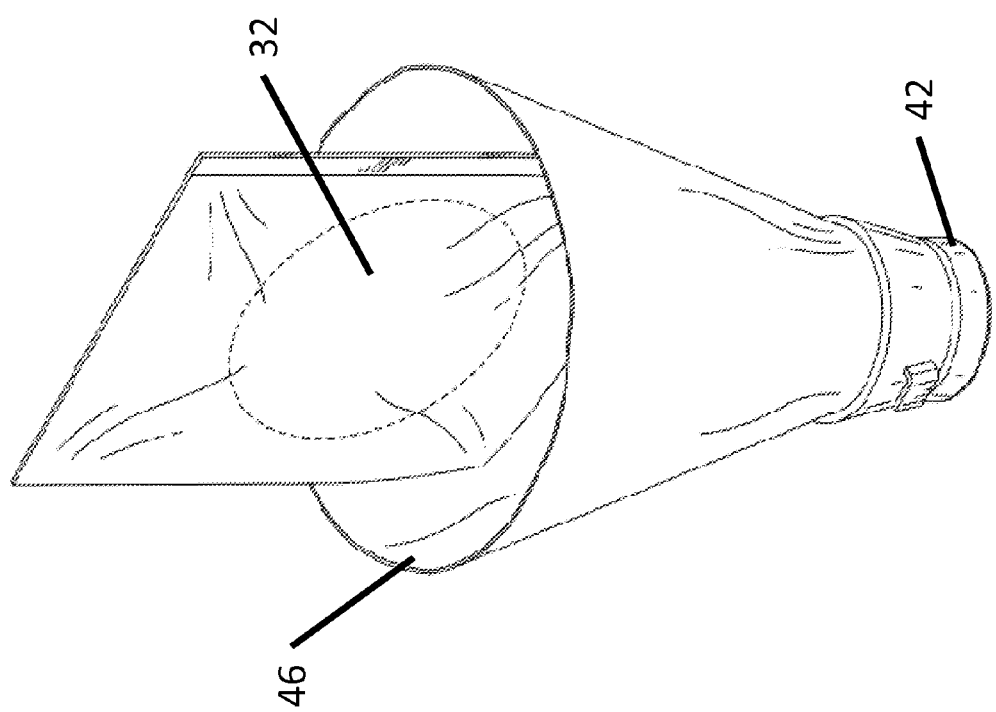

FIG. 6: Front perspective view of a short guide adapter and coupling member combined with a prosthesis manipulation pouch.

Figure 7:
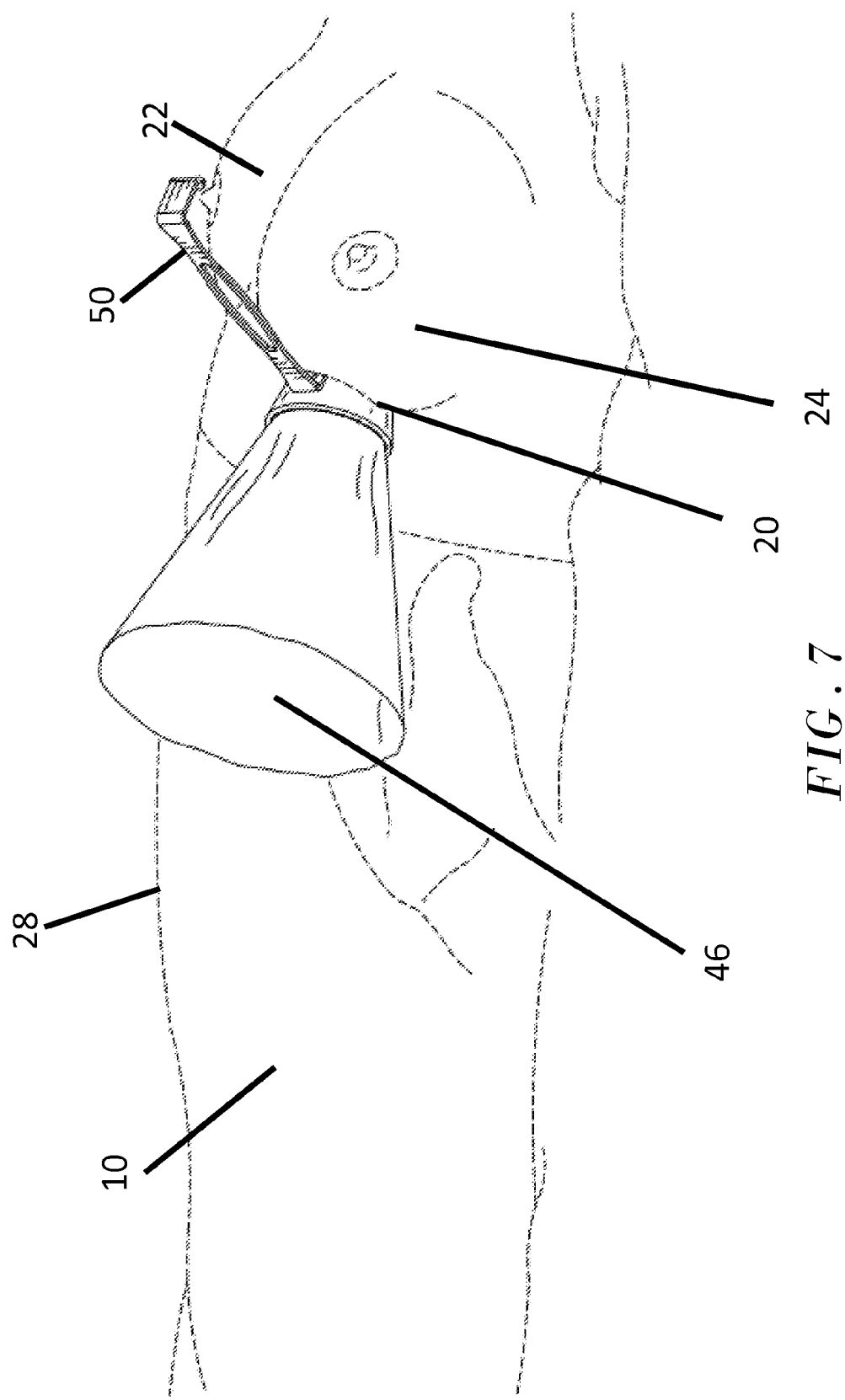

FIG. 7: Front perspective view of a short guide adapter in a patent incision after being rotated into the coupling catch.

Figure 8:
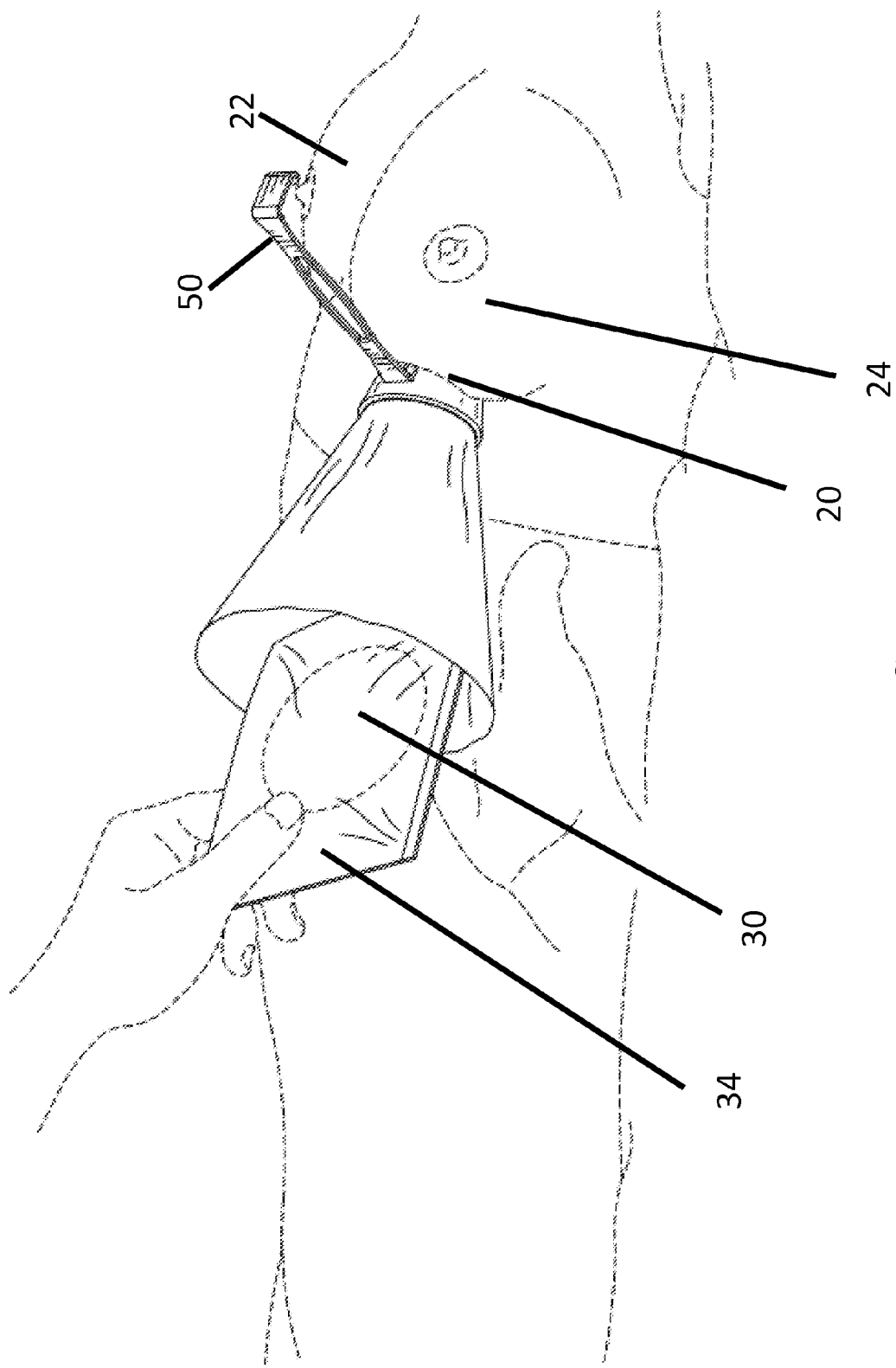

FIG. 8: Front perspective view of a short guide adapter in a patent incision and rotated into the coupling catch while the surgeon uses the manipulation pouch to move the prosthesis into the patient cavity.

KEY TERMS distal: the most distant portion from the point of attachment to the main body
inferior: closer to the feet
lateral: a position substantially located in any side of the longitudinal position of a patient's supine position
longitudinal: a lengthwise, or the longest, direction related to the patient's supine position
proximal: the closest portion from the point of attachment to the main body
superior: closer to the head of the body

REFERENCE NUMERALS IN DRAWINGS 10 patient
20 patient's incision
22 patient's breast
24 patient's cavity, patient's pocket
28 patient's skin tissue
30 prosthesis
32 breast implant
34 prosthesis manipulation pouch; pouch
36 pouch opening, pouch proximal opening
37 pouch sealed edges
38 pouch interior
40 guide member
42 guide adapter proximal end
43 guide proximal opening
44 guide distal end
46 guide distal opening
48 guide inner surface
49 semi-rigid receptacle
50 retractor
52 retractor handle
54 retractor handle distal end
56 retractor handle distal end lip
58 retractor handle proximal end
59 retractor proximal end lip
60 coupling member
62 coupling distal end, distal opening
64 coupling proximal end, proximal opening
70 coupling catch, "L" shaped
72 coupling catch long segment
74 coupling catch short segment
80 lubricant

DETAILED DESCRIPTION OF THE DRAWINGS

Referring to the drawings, in which like numerals represent like elements,

FIG. 1

Turning to FIG. 1, the illustrations depicting a prosthesis manipulation pouch 34. A pouch 34 assembly comprises sealed edges 37, a proximal pouch opening 36 leading to the pouch interior 38. In the preferred embodiment, the pouch 34 shape is a quadrilateral with three (3) sealed edges 37 and an opening 36 on the fourth edge. Another embodiment is an ellipsoid with an opening 36 large enough for prosthesis 30 to pass from the pouch interior 38 to guide member 40. The pouch interior 38 holds the prosthesis 30 and lubricant 80. The pouch 34 may be manufactured with a clear flexible material to allow the surgery to observe the prosthesis 30 during manipulation. In another embodiment, the manufacturer may add color to the flexible pouch 34 so it is more easily observed through the guide member 40 while pushing the prosthesis 30 through the guide 40. The prosthesis manipulation pouch 34 may be shipped with the prosthesis 30 and lubricant 80 in the pouch interior 38. In another embodiment, the surgeon would place the lubricant 80 and prosthesis 30 in the pouch 34 prior to the surgery. The lubricant 80 may also act as an antibiotic solution.

FIG. 2

Referring now to FIG. 2, the drawings show a single catch 70 rotating coupling member 60. A coupling member 60 assembly comprises distal end and opening 62, a proximal end and opening 64, an "L" shaped coupling catch 70. The coupling member 60 serves to stabilize a guide member 40, prevent the breast implant 32 from touching the patient skin tissue 28, and prevent the incision 20 from tearing while passing the prosthesis 30 into the patient cavity 24.

In a preferred embodiment, the coupling member 60 is shipped to the surgeon with the guide member's 40 tunnel-shaped semi-rigid receptacle 49 attached to the distal end 62 of the coupling member 60. In another embodiment, the semi-rigid receptacle 49 is assembled to the coupling member 60 by the surgeon. To assemble the apparatus, the semi-rigid receptacle 49 is inserted into the coupling member 60 and secured thereto. Double sided surgical tape can be used to couple the proximal end 42 of the semi-rigid receptacle 49 inside of the coupling member distal end 62. Alternatively, the receptacle 49 can be coupled to the coupling member 60 by glue or adhesive, heat bonding or other coupling mechanism.

The coupling member 60 has one coupling catch 70 to attach to a retractor 50. The coupling catch 70 is attached to the coupling member 60 by the coupling catch short segment 74. The short segment 74 acts as a stop when the coupling member 60 is rotated inside the incision 20 into the retractor handle proximal end 58. The coupling catch short segment 74 supports a perpendicular coupling catch long segment 72. The long segment 72 holds the retractor 50 in a snug interference fit against the coupling member 60.

FIGS. 3-6

FIGS. 3-6 depict the coupling member 60 assembled as a portion of a guide member 40. In FIG. 3, the semi-rigid receptacle 49 is generally frusto-conical in shape, having proximal and distal ends 42, 44. The proximal and distal ends 42, 44 each have openings with the distal opening 46 being larger in diameter than the proximal opening 43.

A semi-rigid receptacle 49 is made of a sheet material such as plastic. For example, a stiff nylon can be used. The plastic may be strengthened or reinforced with fiber. The semi-rigid receptacle 49 is not flexible in order to maintain the position of the prosthesis 30 and direct it through the coupling member 60 and into the patient pocket 24. The semi-rigid receptacle 49 may be clear, or semi-transparent, in color to allow observation of the prosthesis 30 moving from the pouch 34 into the patient cavity 24.

A coating of surgical lubricant 80 can be used on the inner surface 48. As an alternative, the semi-rigid receptacle 49 can be provided with a coating that becomes slick when wet. In still another alterative, the prosthesis 30 can be provided with a slick surface, such as a surgical lubricant 80.

The coupling member 60 is generally frusto-conical in shape and has a distal end 62 and a proximal end 64. The distal and proximal end 62, 64 have respective openings with the distal 62 opening being larger in diameter than the proximal end opening 64.

The proximal 64 portion of the coupling member 60 can have a short section extending from the proximal end 64 toward the distal end 62, which section has a constant inside diameter. Alternatively, the interior of the coupling member 60 can have a sloped configuration all the way to the proximal end 64.

FIGS. 4 and 5 show the assembly of the retractor 50 removably into the guide member 40. The retractor 50 assembly comprises a handle 52 located in the center, a retractor distal end 54, distal end lip 56, proximal end 58, and proximal end lip 59. The retractor 50 can have various shapes and sizes to match the particular application. The handle 52 of the retractor 50 is bent or angled on the ends 54, 58 relative to the intermediate portion. This is so that when the retractor 50 is coupled to the coupling member 60, the retractor 50 extends laterally from the guide member 40, as shown in FIG. 5, so as not to interfere with the surgeon manipulating the prosthesis manipulation pouch 34 inside the guide member 40. The retractor handle 52 is used for the insertion of the retractor 50 into the patient 10 and coupling the retractor 50 to the coupling member 60. The proximal end 58 in the retractor 50 has a lip 59 that is angled relative to the end 58. The proximal end 58 of the retractor 50 form an interference fit with the coupling catch 70. The retractor 50 is made of metal, such as stainless steel.

The proximal end 58 is structured and arranged to be inserted through the incision 20 into a cavity 24 of a patient 10. The proximal end lip 59 helps maintain the proximal end 58 of the retractor 50 beneath skin tissue 28 of a patient 10. The guide member proximal end 42 is then placed into the patient's incision 20 so that the coupling catch 70 remains outside of the incision 20. The surgeon then rotates the guide member 40 until the catch 70 forms an interference fit with the retractor 50, as in FIGS. 4-5.

In FIG. 6, the prosthesis 30 and prosthesis manipulation pouch 34 is located in the guide member 40. The manipulation pouch 34 is flexible and one preferred embodiment is clear in color. A pocket or cavity 24 is located under the skin tissue 28, which cavity 24 is to receive the prosthesis 30. Inside the guide member 40, the pouch 34 and prosthesis 30 are squeezed and/or twisted to force the prosthesis 30 toward the proximal end 64 of the coupling member 60, and into the cavity 24. The prosthesis 30 deforms to fit through the proximal end opening 42.

FIGS. 7-8

Finally, turning to FIGS. 7-8 depicting a short guide member 40 and coupling member 70 combined with the use of a prosthesis manipulation pouch 34 on a patient 10.

The patient 10 is placed in a supine position and an incision 20 is made. In the figures, the incision 20 is made in the inferior breast 22 crease. A retractor 50 is then inserted to open the incision 20 and hold the incision 20 open. The surgeon then forms a cavity 24 in one of two places under the breast 22: subglandular (between the breast 22 tissue and pectoralis muscle) or subpectoral (under the pectoralis muscle,) which cavity 24 is to receive the prosthesis 30.

The proximal ends of the retractor 58 is inserted into the incision 20 and located under the skin tissue 28 and moved to open the incision 20. The coupling member proximal end 64 is inserted into the now open incision 20 with the coupling catch 70 above the skin 28. The surgeon rotates the guide member 40 until the catch 70 forms an interference fit with the retractor 50, as in FIGS. 7-8.

In FIG. 8, the prosthesis 30 and prosthesis manipulation pouch 34 is located in the guide member 40. Inside the guide member 40, the pouch 34 and prosthesis 30 are squeezed and/or twisted to force the prosthesis 30 toward the proximal end 64 of the coupling member 60, and into the cavity 24. The prosthesis 30 deforms to fit through the proximal end opening 42 of the guide member 40.

Once the prosthesis 30 is located inside the cavity 24, the retractor 50 is uncoupled from the coupling member 60 by relative rotation between the coupling member 60 and the retractor 50. The guide member 40 is then removed from the incision 20, followed by the retractor 50. The incision 20 can then be closed.

If the coupling member 60 and guide member 40 are designed for single use, they are disposed of. If either the coupling member 60 or guide member 40 are designed for reuse, they are subjected to sterilization procedures. An advantage of the insertion apparatus and method is that the implant 32 and insertion apparatus can be properly sized with respect to each other. A manufacturer of implants 32 can provide the properly sized apparatus with the implant 32. The use of the coupling member 60 acts as a sizing cuff on the end of the guide member 40. The size of the coupling member 60 is matched to the size of the implant 32. For example, some implants 32 are physically large and require a coupling member 60 with a larger diameter proximal and distal opening 62, 64, while other implants 32 are physically smaller and can use a coupling member 60 with smaller openings 62 64. By matching the insertion apparatus to the size of the implant 32, the chance that the implant 32 will be damaged by excessive squeezing and stress is minimized. The implant 32 is subject to damage if the implant 32 is mishandled.

Possible mishandling includes subjecting the implant 32 to undue stresses or pressures, such as may be caused by attempting to squeeze the implant 32 through an opening that is too small. A surgeon may make an incision 20 in the patient 10 that is too small for the implant 32 and thus much force is required to squeeze the implant 32 into the cavity 24. With the apparatus, the implant 32 is protected from undue squeezing by the provision of the properly sized apparatus. A surgeon need not guess at what the proper size opening should be for the specific implant 32. The major complication with implants 32 is capsular contracture thought to be due to sub-clinical infection. Sub-clinical infection is most likely caused by pushing the implant 32 through the skin incision 20, dragging natural skin 28 bacteria (still present after proper skin 28 preparation) into the pocket 24 surgically created for the implant 32. Use of this device prevents the implant 32 from coming in contact with the skin tissue 28 during the insertion process.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

In the foregoing description, and the following claims, method steps and/or actions are described in a particular order for the purposes of illustration. It should be appreciated that in alternate embodiments, the method steps and/or actions may be performed in a different order than that described. Additionally, the methods described above may be embodied in machine-executable instructions stored on one or more machine-readable mediums, such as disk drives, thumb drives or CD-ROMs. The instructions may be used to cause the machine (e.g., computer processor) programmed with the instructions to perform the method. Alternatively, the methods may be performed by a combination of hardware and software. While illustrative and presently preferred embodiments of the invention have been described in detail herein, it is to be understood that the inventive concepts may be otherwise variously embodied and employed, and that the appended claims are intended to be construed to include such variations, except as limited by the prior art.

Benefits, other advantages, and solutions to problems have been described herein with regard to specific embodiments. However, the advantages, associated benefits, specific solutions to problems, and any element(s) that may cause any benefit, advantage, or solution to occur or become more pronounced are not to be construed as critical, required, or essential features or elements of any or all the claims of the invention. As used herein, the terms "comprises", "comprising", or any other variation thereof, are intended to cover a non-exclusive inclusion, such that a process, method, article, or apparatus composed of a list of elements that may include other elements not expressly listed or inherent to such process, method, article, or apparatus.

ADVANTAGES

From the description above, a number of advantages become evident for the "Prosthesis Manipulation Pouch." The present invention provides all new benefits for participating parties including patients and surgeons:
 a) allows patient's a lower risk of complications;
 b) allows patient's a more discrete incision size;
 c) allows patient's a quicker recovery;
 d) allows patient's a more comfortable recovery;
 e) allows doctors a true "no touch" method for prosthesis insertion;
 f) allows doctors a secure placement of the device within the incision;
 g) allows doctors a simplified insertion process;
 h) allows doctors to avoid a tearing of the proximal end of the device when applying pressure to the prosthesis.

The invention claimed is:

1. A system for inserting a prosthesis through an incision into a surgical cavity, comprising:
 a. a prosthesis;
 b. a guide member comprising:
  (i) a semi-rigid receptacle comprising a proximal opening and a distal opening, the distal opening being larger than the proximal opening, the receptacle being semi-rigid and structured and arranged to receive the prosthesis;
  (ii) a coupling member comprising a proximal opening and a distal opening, the distal opening being larger than the proximal opening, the proximal end of the semi-rigid receptacle being located inside of the coupling member and assembled to the coupling member distal end opening; and
  (iii) a coupling catch for removably coupling to a retractor, the coupling catch having a short segment attached to the coupling member and supporting a long segment;
 c. the retractor that removably couples to the coupling member, the retractor having a proximal end that is adjacent to the coupling member proximal end and is structured and arranged to engage an edge of a surgical cavity opening, the proximal end of the retractor being fixed relative to the coupling member once the retractor has been coupled to the coupling member; and
 d. a prosthesis manipulation pouch, the prosthesis manipulation pouch being flexible and arranged to deliver the prosthesis into the semi-rigid receptacle.

2. The system of claim 1, wherein the prosthesis manipulation pouch is shaped as a quadrilateral with three sealed edges and an opening on a fourth edge.

3. The system of claim 1, wherein the prosthesis manipulation pouch is shaped as an ellipsoid with an opening for the prosthesis to pass from a pouch interior to the guide member.

4. The system of claim 1, wherein the prosthesis manipulation pouch is located in the guide member.

* * * * *